United States Patent
Pletcher et al.

(10) Patent No.: US 12,318,005 B2
(45) Date of Patent: Jun. 3, 2025

(54) SEATING APPARATUS

(71) Applicants: Stan Pletcher, Niles, MI (US); Sam Pletcher, Indianapolis, IN (US)

(72) Inventors: Stan Pletcher, Niles, MI (US); Sam Pletcher, Indianapolis, IN (US)

(*) Notice: Subject to any disclaimer, the term of this patent is extended or adjusted under 35 U.S.C. 154(b) by 449 days.

(21) Appl. No.: 17/969,722

(22) Filed: Oct. 20, 2022

(65) Prior Publication Data

US 2024/0130531 A1 Apr. 25, 2024
US 2024/0225286 A9 Jul. 11, 2024

(51) Int. Cl.
  *A47C 1/032* (2006.01)
  *A47C 3/30* (2006.01)
  *A47C 7/02* (2006.01)
  *A61B 90/60* (2016.01)
  *A47B 13/02* (2006.01)

(52) U.S. Cl.
  CPC ............ *A47C 1/03255* (2013.01); *A47C 3/30* (2013.01); *A47C 7/029* (2018.08); *A61B 90/60* (2016.02); *A47B 2013/025* (2013.01)

(58) Field of Classification Search
  CPC ....... A47C 1/03255; A47C 3/30; A61B 90/60; A47B 2013/025
  USPC ...................... 297/16.2, 17, 314, 344.19, 461
  See application file for complete search history.

(56) References Cited

U.S. PATENT DOCUMENTS

| | | | | |
|---|---|---|---|---|
| 1,961,530 A | * | 6/1934 | Spanenberg | B60N 2/39 297/314 X |
| 2,132,291 A | * | 10/1938 | Miklos | A47C 9/002 297/314 X |
| 4,074,887 A | * | 2/1978 | Hale | F16M 11/046 248/404 |
| 4,136,908 A | * | 1/1979 | Crayne | A47C 1/11 297/188.21 |
| 4,163,536 A | * | 8/1979 | Heller | A61C 19/00 248/118 |
| 4,552,404 A | * | 11/1985 | Congleton | A47C 9/005 297/330 X |
| 4,753,407 A | * | 6/1988 | Brock | A47C 1/11 248/163.1 |
| 4,865,382 A | * | 9/1989 | Marshall | A47C 9/025 297/195.11 |
| 4,889,383 A | * | 12/1989 | Jones | A47C 4/52 297/17 X |

(Continued)

FOREIGN PATENT DOCUMENTS

| | | | | | |
|---|---|---|---|---|---|
| CN | 109223198 A | * | 1/2019 | | A47C 3/24 |
| DE | 2545969 B1 | * | 2/1978 | | A61B 90/60 |

*Primary Examiner* — Rodney B White
(74) *Attorney, Agent, or Firm* — Alloy Patent Law; Walker Griffin Weitzel (57) ABSTRACT

Presented is a seating apparatus that is enabled to allow a doctor or a surgeon to achieve an appropriate sitting posture during surgery. The seating apparatus includes a seat mount, a strut, a back-rest, a pedal, a seat and a support base. The seat is connected to the seat mount through a fastening means such that the seat is suspended over the seat mount leaving a gap between the seat and the seat mount. The pedal is operatively coupled to a lower end of the strut and the pedal is configured to adjust height of the seat in a hands-free manner. The seating apparatus is modular and it provides an option to user to easily disassemble various components of seating apparatus for easy portability of the seating apparatus.

15 Claims, 4 Drawing Sheets

(56) References Cited

U.S. PATENT DOCUMENTS

| | | | | | |
|---|---|---|---|---|---|
| 4,890,882 | A | * | 1/1990 | Harrington | A47C 4/52 |
| | | | | | 297/17 X |
| 5,366,275 | A | * | 11/1994 | Sulzer | A47C 7/004 |
| | | | | | 297/344.19 X |
| 5,433,502 | A | * | 7/1995 | Condorodis | A47C 4/03 |
| | | | | | 297/17 X |
| 5,505,524 | A | * | 4/1996 | Drumwright | A47C 7/004 |
| | | | | | 297/17 X |
| 6,224,154 | B1 | * | 5/2001 | Stoki | A61B 90/60 |
| | | | | | 297/344.18 |
| 7,100,983 | B1 | * | 9/2006 | Gant | A47C 3/025 |
| | | | | | 297/314 X |
| 7,789,463 | B2 | * | 9/2010 | Gang | A47C 9/002 |
| | | | | | 297/314 X |
| 7,922,247 | B2 | * | 4/2011 | Dickie | A47C 7/14 |
| | | | | | 297/314 X |
| 8,029,060 | B2 | * | 10/2011 | Parker | A47C 7/004 |
| | | | | | 297/314 X |
| 8,152,236 | B1 | * | 4/2012 | Romero | A47D 1/10 |
| | | | | | 297/17 X |
| 2007/0216209 | A1 | * | 9/2007 | Kuenzel | B63B 29/06 |
| | | | | | 297/344.12 |
| 2009/0243345 | A1 | * | 10/2009 | Carter | A47C 7/407 |
| | | | | | 297/16.2 |
| 2009/0261642 | A1 | * | 10/2009 | Dickie | A47C 9/002 |
| | | | | | 297/314 |
| 2016/0081478 | A1 | * | 3/2016 | Ehrenleitner | A47C 3/18 |
| | | | | | 297/314 X |
| 2018/0303694 | A1 | * | 10/2018 | Steenstra Toussaint | |
| | | | | | A61B 17/00 |

* cited by examiner

SEATING APPARATUS

TECHNICAL FIELD

The present invention generally relates to a seating apparatus and more particularly, the present invention relates to an adjustable seating apparatus that provides hands-free seat adjustment. Further, the seating apparatus is modular and it provides an option for a user to easily disassemble various components of the seating apparatus for easy portability of seating apparatus.

BACKGROUND

Conventional chairs and stools are required to be adjusted for achieving various height settings for a variety of reasons. The user may require raising or lowering the seat depending on their own height or function that they wish to perform while being seated. There are various means to adjust the seat that involves hand-assistance to achieve the purpose of height adjustment of the seat. The conventional means of seat adjustment are not effective when it comes to the sitting arrangements used while performing surgeries as they invariably require hand usage for height adjustments, which is problematic for medical professionals working in a sterile environment.

There are various types of surgeries that are commonly performed worldwide. While performing the surgeries, the surgeon requires a user-friendly zone or area to perform the surgery efficiently. User-friendly zone enables the surgeon to access various tools and apparatuses that are used while performing surgeries. Further, the surgeon should feel comfortable in any of the sitting postures while performing surgeries as it eliminates the possibility of any mishap due to the surgeon or doctor's fatigue. The surgeon should be able to adjust the seat without any difficulty. There are various solutions for providing comfort to the surgeon during their work in an operating room.

While performing surgeries, there may be certain scenarios for which the surgeon may require to adjust his/her seat efficiently. The surgeon may require reaching to a higher point of operation during surgery; consequently, he may require lifting the sitting arrangement up to a certain height. Similarly, when the surgeon requires operating at certain lower heights, he/she would require lowering the sitting arrangement to achieve the required level that would help to perform the surgeries efficiently and without any fatigue. Further, the seating arrangements are required to be transported across various places depending on the requirement of the user. Often, a surgeon needs to travel to remote locations and then perform surgical operations while comfortably sitting in a seating arrangement. Thus, a seating arrangement that could be capable of being easily disassembled, stored for later use, easily transported, and then easily assembled on the required location is ideally required.

The existing solutions related to sitting arrangements used in an operation room are limited to providing user-friendly seat adjustments while performing surgeries. Further, the portability of existing sitting arrangements is difficult due to the structure of the seating arrangements.

In the light of the foregoing, there is a need for a relatively easy to use and inexpensive solution that would allow a surgeon to adjust the sitting arrangement while performing surgeries. Further, the seating apparatus should be modular and it should provide an option for the user to easily disassemble various components of the seating apparatus for easy portability.

SUMMARY

It is an objective of the present invention to provide a seating apparatus that allows easy adjustment for seat height.

It is an objective of the present invention to provide a seating apparatus that enables the height adjustment of the seat in a hands-free manner.

It is another objective of the present invention to provide a foot-operated pedal that enables the user to adjust the seat height of the seating apparatus.

It is another objective of the present invention to provide a seating apparatus with a seat mount that is configured to support a canvas of the seat leaving a gap or space between the canvas and the seat mount.

It is an objective of the present invention to provide a seating apparatus that is portable and can be easily disassembled for ease of transportation.

It is an objective of the present invention to provide a modular seating apparatus that provides an option for the user to easily disassemble various components of the seating apparatus for easy portability.

It is an objective of the present invention to provide a seating apparatus that can be easily customized depending on the requirement of the user.

Embodiments of the present invention disclose a seating apparatus comprising a seat mount. An upper end of a strut is connected to the seat mount and a seat is connected to the seat mount. The seat mount comprises a plurality of suspension arms projecting outward from a mounting plate of the seat mount, wherein the seat is connected to the plurality of suspension arms of the seat mount through at least one fastening means such that the seat is at least partially suspended over the seat mount leaving a gap between the seat and the mounting plate of the seat mount. A pedal is cooperatively coupled to a lower end of the strut; and the pedal is configured to adjust the height of the seat in a hands-free manner by adjusting the height of the strut. The seating apparatus is configured to be modular to enable user to easily disassemble the seating apparatus for easy portability of the seating apparatus.

In an embodiment, the seating apparatus comprises a back-rest which comprises two support rods and a flexible web.

In an embodiment, the seat mount comprises four suspension arms.

In an embodiment, the seat mount comprises three suspension arms.

In an embodiment, an adjuster mechanism is installed on each of the plurality of legs to enable each of the plurality of legs to be removed from the support base and/or adjust in overall length.

In an embodiment, a locking element is removably connected to at least one of plurality of legs to stack and/or lock a plurality of legs after the plurality of legs are removed from the support base.

In an embodiment, the locking element is a carabiner.

In an embodiment, the seating apparatus can be selectively positioned between a deployed mode and a storage mode.

In an embodiment, the fastening means is selected from group consisting of a cotter pin, rivet, grommet, clevis pin, screw-nut fastener, snap-fit coupling, friction couplings, clamps and pins.

Embodiments of the present invention further disclose a seating apparatus comprising a seat mount, a back-rest and a strut cooperatively positioned between the seat mount and a support base. The seat mount comprises a plurality of suspension arms and a mounting plate. A seat is connected to the plurality of suspension arms of the seat mount through atleast one fastening means. The back-rest comprises two support rods and a flexible web. The support base comprises a plurality of legs, a plurality of wheels, an adjuster mechanism installed on each of the plurality of legs. The seating apparatus is configured to be selectively positioned between a deployed mode and a storage mode. In the storage mode, the plurality of legs are removed from the support base by using the adjuster mechanism, the seat is rolled to occupy minimal space, the plurality of suspension arms are detached from the mounting plate of the seat mount, the plurality of suspension arms are further detached from the seat and/or two support rods by unfastening the fastening means, and the flexible web is rolled to occupy minimal space.

In an embodiment, a locking element is configured to stack and/or lock a plurality of legs after the plurality of legs are removed from the support base in the storage mode.

In an embodiment, the locking element is a carabiner.

In an embodiment, the plurality of suspension arms projects outward from the mounting plate of the seat mount.

In an embodiment, the seat is connected to the plurality of suspension arms of the seat mount through at least one fastening means such that the seat is at least partially suspended over the seat mount leaving a gap between the seat and the mounting plate of the seat mount.

In an embodiment, a pedal is cooperatively coupled to a lower end of the strut; and the pedal is configured to adjust the height of the seat in a hands-free manner by adjusting height of the strut.

In an embodiment, an adjuster mechanism is further configured to adjust the overall length of the support base.

The present invention provides a surgeon stool or the like that prevents or eliminates any infection caused by hand touching, for the purpose of seat adjustments, while performing surgeries in an operation room. These and other features and advantages of the present invention will become apparent from the detailed description below, in light of the accompanying drawings.

DETAILED DESCRIPTION

Before describing the present invention in detail, it should be observed that the present invention utilizes a combination of components or processes, which constitutes a seating apparatus. Accordingly, the components or processes have been represented, showing only specific details that are pertinent for an understanding of the present invention so as not to obscure the disclosure with details that will be readily apparent to those with ordinary skill in the art having the benefit of the description herein. As required, detailed embodiments of the present invention are disclosed herein; however, it is to be understood that the disclosed embodiments are merely exemplary of the invention, which can be embodied in various forms. Therefore, specific component level details and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

References to "one embodiment", "an embodiment", "another embodiment", "one example", "an example", "another example" and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment. The words "comprising", "having", "containing", and "including", and other forms thereof, are intended to be equivalent in meaning and be open ended in that an item or items following any one of these words is not meant to be an exhaustive listing of such item or items or meant to be limited to only the listed item or items.

The seating apparatus will now be described with reference to the accompanying drawings, particularly FIGS. 1-4.

Figure 1:
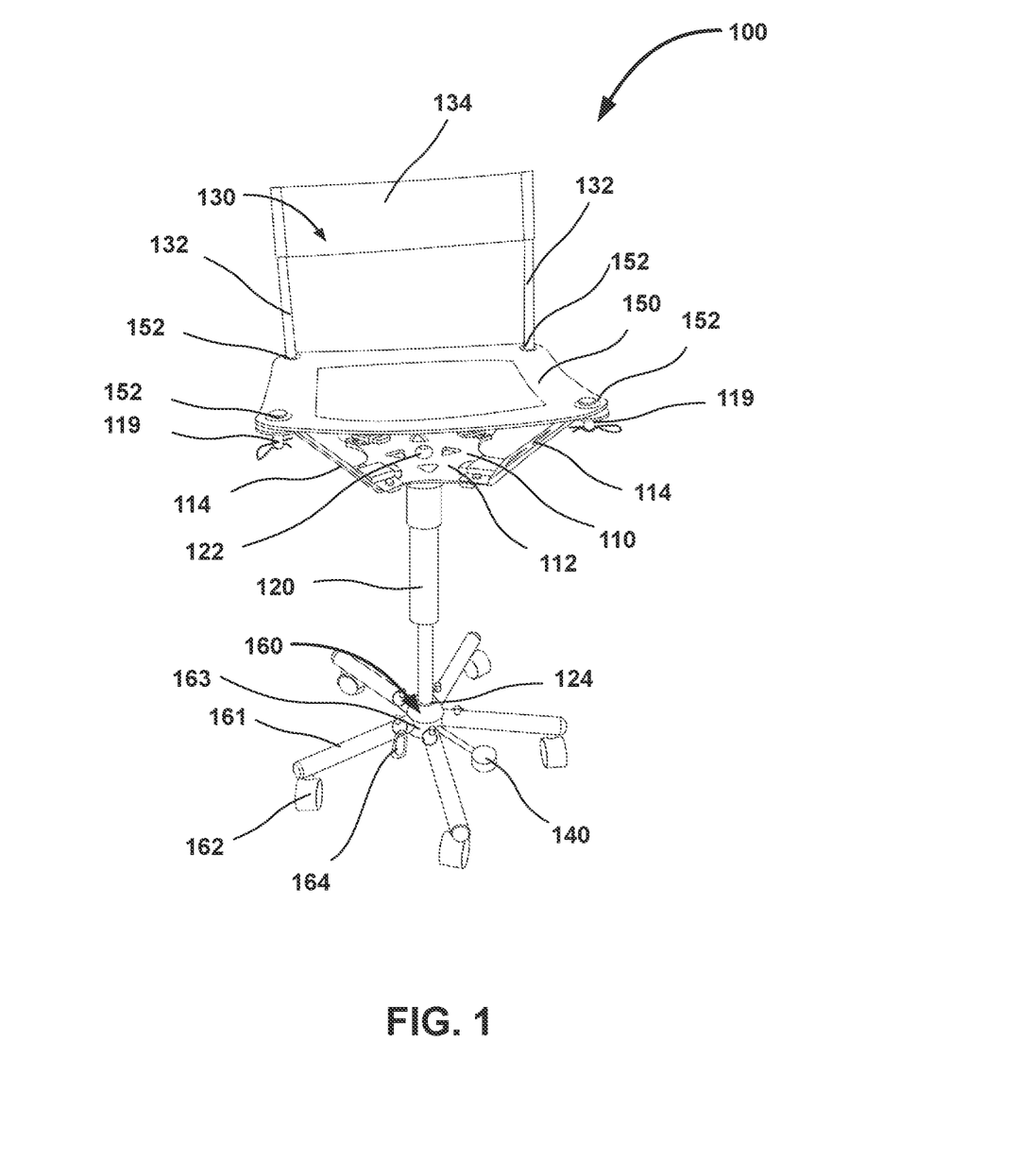
FIG. 1 shows a front perspective view of a seating apparatus, according to an embodiment of the invention.

FIG. 1 illustrates a front perspective view of a seating apparatus 100. The seating apparatus 100 enables a doctor or a surgeon to achieve an appropriate sitting posture during surgery. The seating apparatus 100 includes a seat mount 110, a strut 120, a back-rest 130, a pedal 140, a seat 150 and a support base 160. The seat mount 110 further comprises a mounting plate 112 and a plurality of suspension arms 114. The strut 120 of the seating apparatus 100 is a collapsible strut configured to extend and retract vertically. Further, in an embodiment, the strut 120 is inverted to allow for a pedal 140 operated by a foot of surgeon to adjust the seating apparatus 100 by extending and/or retracting the strut 120. The back-rest 130 further comprises two support rods 132 and a flexible web 134 made of materials such as but not limited to: canvas, nylon, polyester, rubber, textile material, and so on. The pedal 140 is a foot operated pedal that eliminates the usage of hands for adjusting the seat height and therefore providing a hands-free operation for seat adjustments while performing surgeries. The seat 150 is made of a material including but not limited to: canvas, nylon, polyester, rubber, textile material, and so on. The seat comprises four holes 152 which are further referred as two front holes 152 and two rear holes 152 (The two front holes 152 and two rear holes 152 are collectively referred as "four holes 152"). The support base 160 comprises a plurality of legs 161, a plurality of wheels 162, an adjuster mechanism 163 on each of the plurality of legs 161 and a locking element 164 removably connected to at least one of plurality of legs 161. The provision of hands-free seat adjustment enabled by the pedal 140 of the seating apparatus 100 ensures no touching of hands for adjusting seats during surgeries that prevents any infection caused by touching in the operation room.

Figure 2:
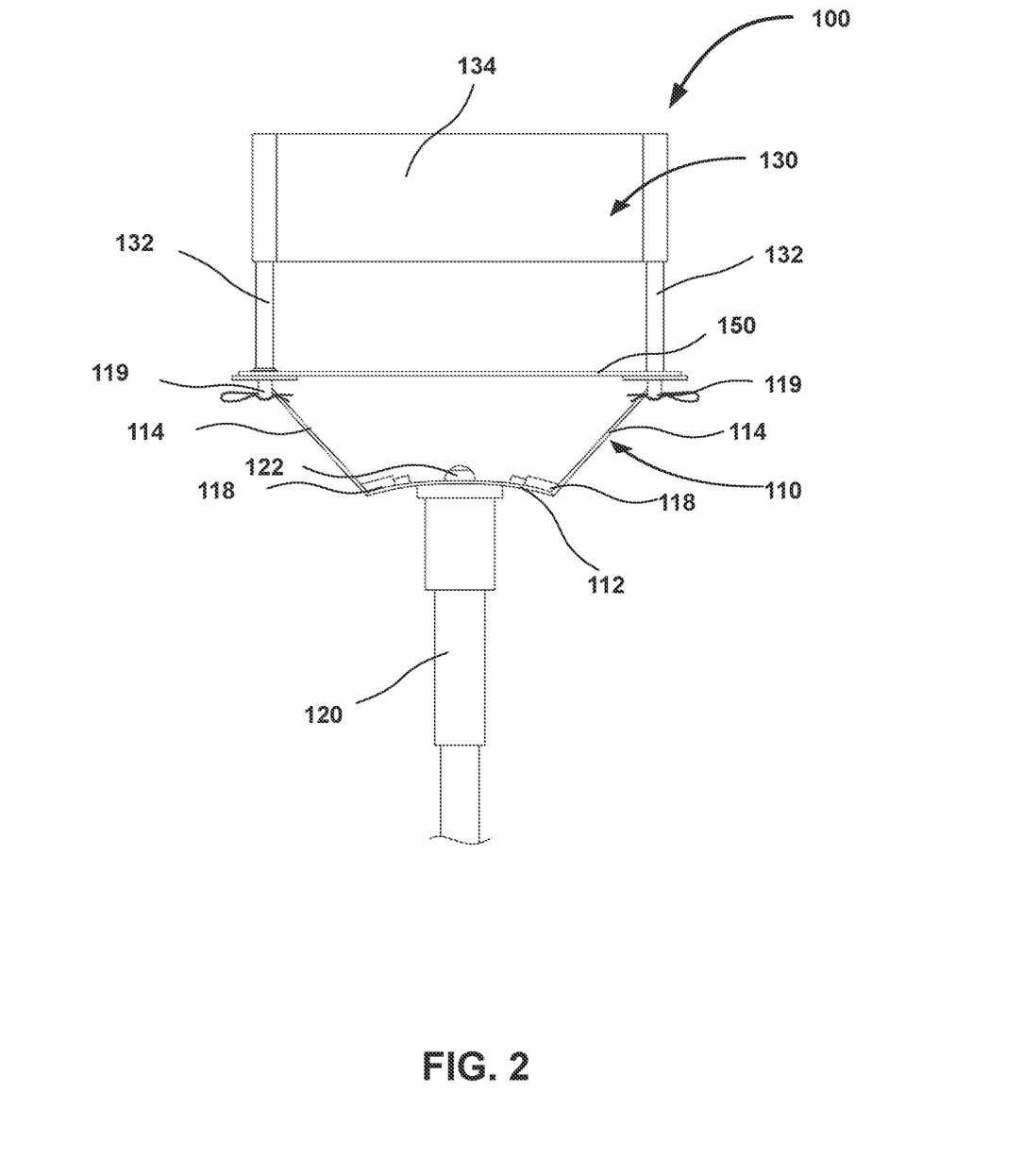
FIG. 2 shows a front view of a seat mount connected to a strut of the seating apparatus, according to an embodiment of the invention.

In an embodiment as shown in FIG. 1 and FIG. 2, the seat mount 110 is trapezoidal shaped which will be described in greater detail in the below description.

The mounting plate 112 of the seat mount 110 is connected to an upper end 122 of the strut 120 through a fastening means 126 (not shown in figures). In an embodiment, the upper end 122 of the strut 120 is a threaded rod or stud that is passed through a hole 113 (FIG. 3) of the mounting plate 112 for fastening the upper end 122 of the strut 120 to the mounting plate 112 of the seat mount 110. The lower end 124 of the strut 120 is cooperatively connected to the support base 160. The pedal 140 is cooperatively coupled to the lower end 124 for adjusting the seating apparatus 100 by extending and/or retracting the strut 120.

Figure 3:
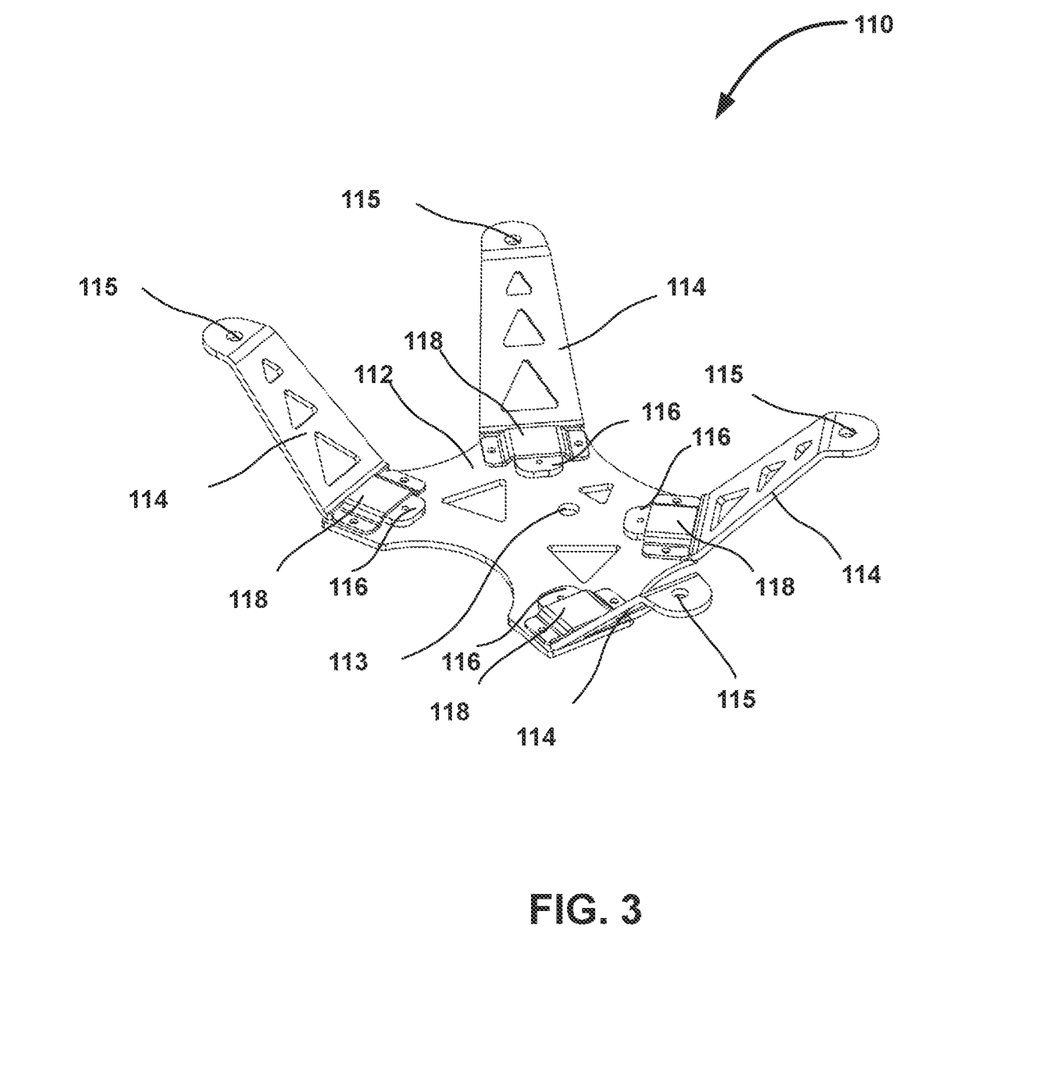
FIG. 3 shows a perspective view of a trapezoidal shaped seat mount with four suspension arms, according to an embodiment of the invention.

The plurality of suspension arms 114 projects outwardly from the mounting plate 112 of the seat mount 110. As seen in FIGS. 1-3, the first end of the suspension arms 114 includes a hole 115 and the seat 150 comprises a plurality of holes 152, which is four in number in FIGS. 1-3. The two fastening means 119 are fastened to the front holes 152 of the seat 150 and the holes 115 of the two front suspension arms 114 such that the seat 150 is substantially suspended over the seat mount 110 leaving a gap between the seat 150 and the mounting plate 112 of the seat mount 110 as can be seen through FIG. 2. In an embodiment, the two fastening means 119 for connecting the first end of the two front suspension arms 114 to the seat 150 is a cotter pin, rivet, grommet, clevis pin, screw-nut fastener, snap-fit coupling, friction couplings, clamps and pins or the like. The first end of the two rear suspension arms 114 further comprises the hole 115 for detachably connecting the two support rods 132 of the back-rest 130 to the holes 115 of the two rear suspension arms 114. The opposite second end of the plurality of suspension arms 114 are detachably connected to the mounting plate 112 of the seat mount 110. The back-rest 130 enables the user to achieve a comfortable or upright sitting posture. The flexible web 134 is connected to the two support rods 132 for providing a support to the lumbar/back of a user.

The support base 160 comprises a plurality of legs 161, a plurality of wheels 162 and an adjuster mechanism 163. The plurality of legs 162 project outwardly from a lower end of the strut 120 in the same plane to provide a stable base for the seating apparatus 100. The adjuster mechanism 163 installed on each of the plurality of legs 161 enables the plurality of legs 161 to be removed from the support base 160 or adjusted in length, depending on the user requirement. In an embodiment, the adjuster mechanism 163 is configured such that the plurality of legs 161 are expanded or retracted up to a pre-defined range. The adjuster mechanism 163 enables the variation in the shape and/or size of the support base 160. In another embodiment, the adjuster mechanism 163 is configured to detach each of the plurality of legs 161 from the support base 160. As seen in FIG. 1, the locking element 164 is a carabiner which is used to stack and/or lock a plurality of legs 161 after the plurality of legs 161 are removed from the support base 160 in storage/ stacking mode. However, other locking element 164 such as but not limited to: cable combination locks, chain locks, U locks and so on could also be employed to serve the same purpose of stacking and locking a plurality of legs 161 after the plurality of legs 161 are removed from the support base 160 in storage/stacking mode. The plurality of wheels 162 are configured to displace the seating apparatus 100 from one place to another while the surgeon is performing surgery in the operation room.

In an embodiment (not shown in figures), the adjuster mechanism 163 is a female-type element having a plurality of threaded holes (not shown in figures). Each of the plurality of legs 161 comprises a threaded shaft element (not shown in figures). Each of the plurality of threaded holes (not shown in figures) is configured to detachably receive a threaded shaft element (not shown in figures) of one of the plurality of legs 161. The threaded connection between the plurality of legs 161 and the adjuster mechanism 163 allows each of the plurality of legs 161 to be removed from the support base 160 and/or adjust in overall length by rotating the plurality of legs 161 relative to the adjuster mechanism 163 and vice versa.

In an embodiment, the seating apparatus 100 is configured to be selectively positioned between a deployed mode as seen in FIG. 1, and a storage mode (not shown in figures). The deployed mode is primarily used during seating by a user. The storage mode allows a provision to fold and/or bring the seating apparatus 100 in a compact size that facilitates easy carriage of the seating apparatus 100 from one place to another.

In an exemplary embodiment, In the storage mode (not shown in figures), the plurality of legs 161 are removed from the support base 160. The locking element 164 further stack and/or lock a plurality of legs 161 after the plurality of legs 161 are removed from the support base 160. Further, In the storage mode, the seat 150 of the seating apparatus 100 is rolled to occupy minimal space. Further, the plurality of suspension arms 114 are detached from the mounting plate 112 of the seat mount 110. Further, the fastening means 119 is unfastened to allow the detachment of the plurality of suspension arms 114 from the seat 150 and/or two support rods 132. Further, the flexible web 134 could be rolled to occupy minimal space by bringing the two support rods 132 close to each other and/or rotating the two support rods 132 relative to one another. The above mentioned steps are exemplary only and the user can bring the seating apparatus 100 in the storage mode by following above mentioned steps in any order deemed fit by the user.

The user can bring back the seating apparatus 100 from the storage mode to a deployed mode (FIG. 1) by merely reversing above mentioned steps with little or no variation.

FIG. 3 illustrates the trapezoidal shaped seat mount 110, according to an embodiment of the present invention. The trapezoidal shaped seat mount 110 is primarily used for quadrilateral shaped seats. The seat mount 110 includes a mounting plate 112 and four suspension arms 114. The four suspension arms 114 are substantially equidistant to each other providing a general trapezoidal shaped seat mount 110. The four suspension arms 114 are further designated as two front suspension arms 114 and two rear suspension arms 114 wherein the two front suspension arms 114 and two rear suspension arms 114 are collectively referred as "four suspension arms 114". The mounting plate 112 comprises a hole 113 for fastening the upper end 122 of the strut 120 to the mounting plate 112 of the seat mount 110 by a fastening means 126 (not shown in figures) as seen in FIG. 1 and FIG. 2. The first end of the suspension arm 114 includes a hole 115 and the second opposite end of the suspension arm 114 includes an extending portion 116. A bracket 118 is detachably connected to the extending portion 116 of the four suspension arms 114 and the mounting plate 112 such that the four suspension arms 114 and the mounting plate 112 are detachably connected to each other. The extending portion 116 of the four suspension arms 114 is detachably connected to the bracket 118 that enables the suspension arm 114 to be removed for stacking/storage purpose. The detachable connection between the suspension arm 114 and the mounting plate 112 is enabled by use of existing mechanical connectors such as but not limited to: screws, rivets and so on. As seen in FIG. 1 and FIG. 2, the two fastening means 119 is fastened to the two front holes 152 of the seat 150 and the holes 115 of the two front suspension arms 114 such that the seat 150 is substantially suspended over the seat mount 110 leaving a gap between the seat 150 and the mounting plate 112 of the seat mount 110 as can be seen through FIG. 2. In an embodiment, the fastening means 119 for connecting the first end of the two front suspension arms 114 to the seat 150 is a cotter pin, rivet, grommet, clevis pin or the like. The first end of the two rear suspension arms 114 further comprises the hole 115 for detachably connecting the two support rods 132 (FIG. 1) of the back-rest 130 to the holes 115 of the two rear suspension arms 114. Each of the two support rods 132 (FIG. 1) passes through a rear hole 152 of the seat 150. Further, each of the two support rods 132 (FIG. 1) have a fastening means (not shown in figures) that enable removable connection between the two rear suspension arms 114 and the two support rods 132 (FIG. 1).

Figure 4:
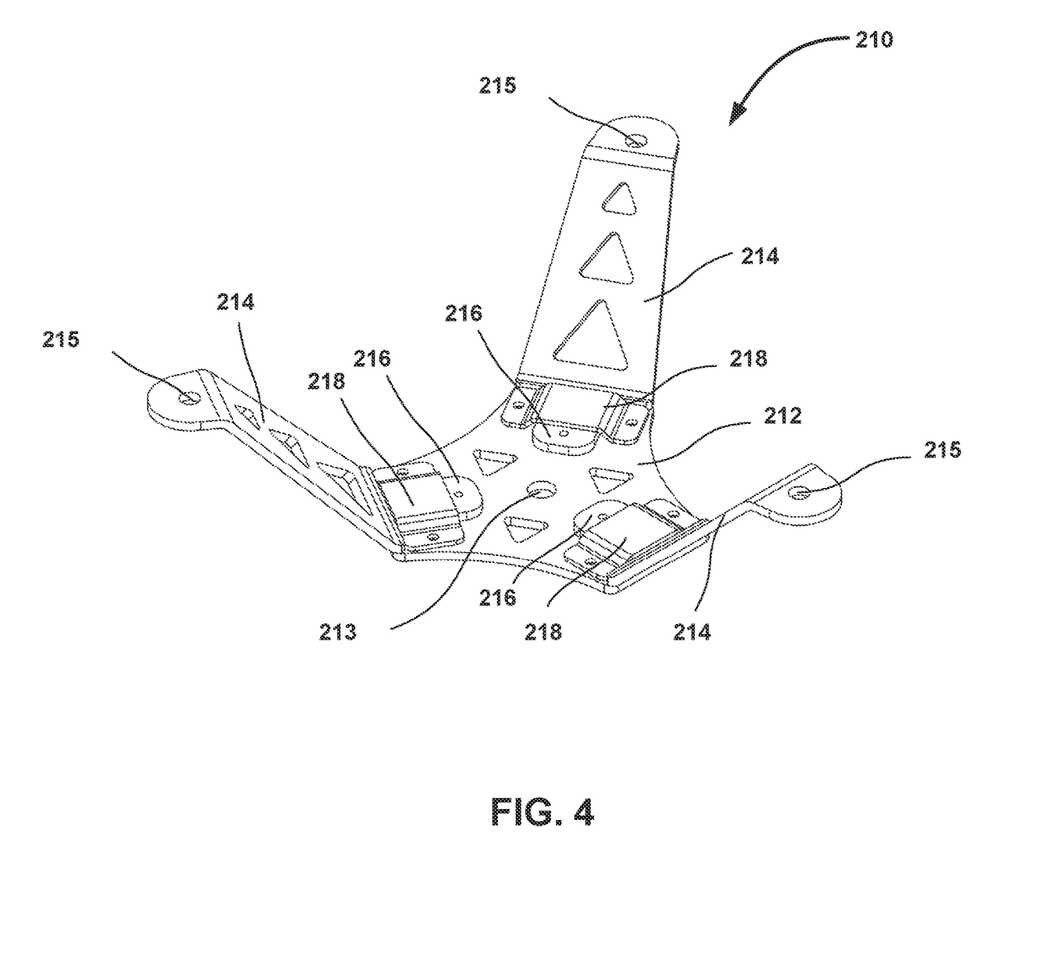
FIG. 4 shows a perspective view of a triangular shaped seat mount with three suspension arms, according to another embodiment of the invention.

FIG. 4 illustrates a triangular shaped seat mount 210, according to another embodiment of the present invention. FIG. 4 is pretty similar to FIG. 3 except for the geometrical modifications that the seat mount has three suspension arms. The triangular shaped seat mount 210 is primarily used for triangular shaped seats. The seat mount 210 includes a mounting plate 212 and three suspension arms 214 that are substantially equidistant to each other providing a general triangular shaped seat mount 210. The three suspension arms 214 are further designated as one front suspension arm 214 and two rear suspension arms 214 wherein the one front suspension arm 214 and two rear suspension arms 214 are collectively referred as "three suspension arms 214". The mounting plate 212 comprises a hole 213 for fastening the upper end 122 of the strut 120 (FIG. 1) to the mounting plate 212 of the seat mount 210 by a fastening means 126 (not shown in figures). The first end of the suspension arm 214 includes a hole 215 and the second opposite end of the suspension arm 214 includes an extending portion 216. A bracket 218 is detachably connected to the extending portion 216 of the suspension arm 214 and the mounting plate 212 such that the three suspension arms 214 and the mounting plate 212 are detachably connected to each other. The extending portion 216 of the three suspension arms 214 is detachably connected to the bracket 218 that enables the three suspension arms 214 to be removed for stacking/ storage purpose. The detachable connection between the suspension arm 214 and the mounting plate 112 is enabled by use of existing mechanical connectors such as but not limited to: screws, rivets and so on. The one fastening means 119 (as seen in FIG. 1 and FIG. 2) is fastened to a front hole 152 (discussed in detail in below description) of the seat 150 and the hole 215 of the one front suspension arm 214 such that the seat 150 (FIG. 1) is substantially suspended over the seat mount 210 leaving a gap between the seat 150 and the mounting plate 212 of the seat mount 210. In an embodiment, the one fastening means 119 (FIG. 1) for connecting the first end of the one front suspension arm 214 to the seat 150 (FIG. 1) is a cotter pin, rivet, grommet, clevis pin or the like. The first end of the two rear suspension arms 214 further comprises the hole 215 for detachably connecting the two support rods 132 (FIG. 1) of the back-rest 130 to the holes 215 of the two rear suspension arms 214.

In an embodiment (not shown in figures), the seat comprises three holes 152 which are further referred to as one front hole 152 and two rear holes 152 (The one front hole 152 and two rear holes 152 are collectively referred to as "three holes 152"). In an embodiment (not shown in figures), Each of the two support rods 132 (FIG. 1) passes through one of two rear holes 152 of the seat 150. Further, each of the two support rods 132 (FIG. 1) have a fastening means (not shown in figures) that enable removable connection between the two rear suspension arms 214 and the two support rods 132 (FIG. 1).

It should be obvious to the one skilled in the art that the various embodiments of seat mount as shown in FIG. 3 and FIG. 4 are pretty similar and could be used interchangeably in the seating apparatus 100. The trapezoidal shaped seat mount 110 shown in FIG. 3 is primarily suited for a quadrilateral shaped seat having four holes 152, while the triangular shaped seat mount 210 shown in FIG. 4 is primarily suited for triangular shaped seat having three holes 152.

In another embodiment, the number of suspension arms 114 projecting from the mounting plate 112 is varied depending upon the shape and size of the seat 150 of the seating apparatus 100. The plurality of suspension arms 114 are set equal to two or more in number depending upon the requirement of the user and/or seat shape. Similarly, in various embodiments, the shape of seat 150 can include but not limited to triangle, quadrilateral, hexagon, circular and so on.

In an embodiment, the strut 120 further includes a locking pin (not shown) for holding the required selected height of the strut 120 of the seating apparatus 100.

In an embodiment, the plurality of legs 161 of the seating apparatus 100 are removably coupled to the support base 160. This allows a provision to fold the seating apparatus 100 in a compact size that facilitates easy carriage of the seating apparatus 100 from one place to another. The seat 150 of the seating apparatus 100 is rollable for easily storing the seating apparatus 100.

The seating apparatus 100 according to various embodiments is suited for performing surgeries. However, the seating apparatus could also be used for other purposes such as but not limited to: camping, sports and office purposes. Further, the seating apparatus 100 is configured to be folded down in a compact state, therefore the seating apparatus may be easily carried along on a journey. Further, the seating apparatus 100 is modular and it provides an option to user to easily disassemble various components of seating apparatus 100 for easy portability when the seating apparatus 100 is not in use i.e. when the seating apparatus 100 is folded in compact state. The various components include but not limited to: a seat mount (110, 210), a strut 120, a back-rest 130, a pedal 140, a seat 150 and a support base 160. The various components could be disassembled from one another and packaged/folded to enable a user to easily transport them from one place to another in compact state.

Although particular embodiments of the invention have been described in detail for purposes of illustration, various modifications and enhancements may be made without departing from the spirit and scope of the invention.

What is claimed is:
1. A seating apparatus (100), comprising:
 a seat mount (110), an upper end (122) of a strut (120) connected to the seat mount (110), a support base (160) comprising a plurality of legs (161), and a seat (150) connected to the seat mount (110);

wherein the seat mount (110) comprises a plurality of suspension arms (114) projecting outward from a mounting plate (112) of the seat mount (110);

wherein the seat (150) is connected to the plurality of suspension arms (114) of the seat mount (110) through at least one fastening means (119) such that the seat (150) is at least partially suspended over the seat mount (110) leaving a gap between the seat (150) and the mounting plate (112) of the seat mount (110);

an adjuster mechanism (163) installed on each of the plurality of legs (161) to enable each of the plurality of legs (161) to be removed from the support base (160) and/or adjust the overall length;

a pedal (140) cooperatively coupled to a lower end (124) of the strut (120), and the pedal (140) is configured to adjust the height of the seat (150) in a hands-free manner by adjusting the height of the strut (120); and wherein the seating apparatus (100) is configured to be modular to enable user to easily disassemble the seating apparatus (100) for easy portability of the seating apparatus (100).

2. The seating apparatus (100) of claim 1, wherein the seating apparatus (100) comprises a back-rest (130) which comprises two support rods (132) and a flexible web (134).

3. The seating apparatus (100) of claim 1, wherein the seat mount (110) comprises four suspension arms (114).

4. The seating apparatus (100) of claim 1, wherein the seat mount (110) comprises three suspension arms (114).

5. The seating apparatus (100) of claim 1 further comprising a locking element (164) removably connected to at least one of plurality of legs (161) to stack and/or lock a plurality of legs (161) after the plurality of legs (161) are removed from the support base (160).

6. The seating apparatus (100) of claim 5, wherein the locking element (164) is a carabiner.

7. The seating apparatus (100) of claim 1, wherein the seating apparatus (100) can be selectively positioned between a deployed mode and a storage mode.

8. The seating apparatus (100) of claim 1, wherein the fastening means (119) is selected from a group consisting of a cotter pin, rivet, grommet, clevis pin, screw-nut fastener, snap-fit coupling, friction couplings, clamps, and pins.

9. A seating apparatus (100), comprising:

a seat mount (110), a back-rest (130), and a strut (120) cooperatively positioned between the seat mount (110) and a support base (160);

wherein the seat mount (110) comprises a plurality of suspension arms (114) and a mounting plate (112);

wherein a seat (150) is connected to the plurality of suspension arms (114) of the seat mount (110) through at least one fastening means (119);

wherein the back-rest (130) comprises two support rods (132) and a flexible web (134);

wherein the support base (160) comprises a plurality of legs (161), a plurality of wheels (162), and an adjuster mechanism (163) installed on each of the plurality of legs (161);

Wherein the seating apparatus (100) is configured to be selectively positioned between a deployed mode and a storage mode; and Wherein in the storage mode, the plurality of legs (161) are removed from the support base (160) by using the adjuster mechanism (163), the seat (150) is rolled to occupy minimal space, the plurality of suspension arms (114) are detached from the mounting plate (112) of the seat mount (110), the plurality of suspension arms (114) are further detached from the seat (150) and/or two support rods (132) by unfastening the fastening means (119), and the flexible web (134) is rolled to occupy minimal space.

10. The seating apparatus (100) of claim 9 further comprising a locking element (164) configured to stack and/or lock a plurality of legs (161) after the plurality of legs (161) are removed from the support base (160) in the storage mode.

11. The seating apparatus (100) of claim 10, wherein the locking element (164) is a carabiner.

12. The seating apparatus (100) of claim 9, wherein the plurality of suspension arms (114) projects outward from the mounting plate (112) of the seat mount (110).

13. The seating apparatus (100) of claim 9, wherein the seat (150) is connected to the plurality of suspension arms (114) of the seat mount (110) through at least one fastening means (119) such that the seat (150) is at least partially suspended over the seat mount (110) leaving a gap between the seat (150) and the mounting plate (112) of the seat mount (110).

14. The seating apparatus (100) of claim 9 further comprising a pedal (140) cooperatively coupled to a lower end (124) of the strut (120); and the pedal (140) is configured to adjust height of the seat (150) in a hands-free manner by adjusting height of the strut (120).

15. The seating apparatus (100) of claim 9, wherein the adjuster mechanism (163) is further configured to adjust the overall length of the support base (160).

* * * * *